(12) United States Patent
Shah

(10) Patent No.: US 6,692,529 B2
(45) Date of Patent: Feb. 17, 2004

(54) HIP REPLACEMENT SYSTEM HAVING FAT LUBRICANT

(76) Inventor: Mrugesh K. Shah, 403 Trails Ct., Houston, TX (US) 77024

(*) Notice: Subject to any disclaimer, the term of this patent is extended or adjusted under 35 U.S.C. 154(b) by 79 days.

(21) Appl. No.: 09/963,627

(22) Filed: Sep. 27, 2001

(65) Prior Publication Data

US 2003/0060891 A1 Mar. 27, 2003

(51) Int. Cl.[7] ............................................... A61F 2/32
(52) U.S. Cl. ................................................. 623/22.13
(58) Field of Search .................... 623/22.11, 22.13, 623/22.14, 22.15, 18.11, 19.12

(56) References Cited

U.S. PATENT DOCUMENTS

| | | | | | |
|---|---|---|---|---|---|
| 3,521,302 A | * | 7/1970 | Muller | .................. | 623/18.11 |
| 3,658,056 A | * | 4/1972 | Huggler et al. | .......... | 623/22.43 |
| 3,683,421 A | * | 8/1972 | Martinie | .................. | 623/22.13 |
| 4,562,598 A | * | 1/1986 | Kranz | .................... | 623/18.11 |
| 5,788,916 A | * | 8/1998 | Caldarise | .................... | 264/122 |
| 5,997,576 A | * | 12/1999 | Copf | ........................ | 623/18.11 |

FOREIGN PATENT DOCUMENTS

EP 0084094 * 7/1983 ............. A61F/1/03

* cited by examiner

Primary Examiner—Cary E. O'Connor
Assistant Examiner—Michael B. Priddy
(74) Attorney, Agent, or Firm—Harrison & Egbert

(57) ABSTRACT

A hip replacement system including a socket having generally hemispherical cavity therein, a ball member cantably affixed within the socket, a stem affixed to the ball member and extending outwardly therefrom, and a lubricant located within a channel formed interior of the stem. The exterior surface of the ball member has at least one opening therein communicating with channel of the stem. The lubricant fills a space between the exterior surface of the ball member and the inner wall of the cavity of the socket. The lubricant is compressed body fat. An inlet is connected to the channel so as to extend outwardly of the stem for allowing the introduction of the lubricant into the channel.

17 Claims, 3 Drawing Sheets

HIP REPLACEMENT SYSTEM HAVING FAT LUBRICANT

BACKGROUND OF THE INVENTION

1. Field of the Invention

The present invention relates to various medical devices used for the replacement of human joints. More particularly, the present invention relates to methods and apparatus for replacing human joints, in particular, hip joints. Additionally, the present invention relates to systems for automatically lubricating artificial joints.

2. Description of Related Art

Prostheses for the replacement of hip joints are already known. Originally, only the ball-end on the head of the femur could be replaced, but it has since proved possible to replace either part of the hip joint, that is to say, the acetabulum or the ball-end on the head of the femur.

The number of those living with hip prostheses is increasing more and more at the present time. The number of implanted artificial hip joints is estimated to be two thousand per day. The further increase of the cases into the millions is accounted for by the fact that the diseases of the hip joints due to wear are increasing numerically along with the rapid rise of the age of the population accompanied by a corresponding development of the medical technique.

Existing techniques for the carrying out of the hip replacement operation are extremely invasive. As such, the patient will require long periods of rehabilitation and long periods of hospital stay. Since a great deal of biological material is removed or replaced in the patient, a great amount of time is required for healing. Furthermore, the operative procedures are very time-consuming and very expensive.

Existing hip replacement techniques initially require the exposure of the femur. The hip must be dislocated so that the level of the neck resection can be measured proximally from the lesser femoral head based on the preoperatively templated measurement. In addition, the center of the femoral head is approximated and marked. A right angle retractor is used to judge the anatomical relationship for the later restoration of leg length and offset. The femoral neck cut is made by using a femoral broach as a template, by using the femoral neck cutting guide, or by using a femoral resection template. The neck cut is made slightly horizontal, which allows the use of the calcar planer to obtain a smooth surface for eventual flush collar-calcar seating.

Following the removal of the femoral head, a partial superior and anterior capsulectomy is performed to allow exposure of the anterior acetabular rim. Hohmann or similar retractors are placed over the anterior rim for retraction of the shaft anteriorly. Posterior and superior Charnley pin retractors are placed in the interval between the capsule and the labrum to allow complete exposure. The acetabular rim is then completely exposed by thorough removal of the acetabular labrum.

Once acetabular exposure has been accomplished, reaming is initiated. Reaming continues until concentric removal of all remaining acetabular cartilage and the exposure of punctate bleeding in the subchondral plate is achieved. The medial landmark for correct depth is the acetabular floor visualized through the acetabular fossa. A cup sizer corresponding to the last reamer used is placed on a handle and inserted into the acetabulum. The acetabular cup sizers are the same size as the actual implant and should fit snugly into the acetabulum.

It is then necessary to insert the cup. To correctly judge the appropriate component position, a down-sized acetabular sizer can be easily inserted and positioned into the acetabulum so as to allow removal of any overhanging anterior, posterior or superior osteophytes. Once these steps have been completed, the correct acetabular shell is locked into the acetabular positioner and driven into a fully seated position. Screws can then be used for supplemental fixation.

After the placement of the acetabular component, attention is then turned to the femur. The femoral canal is identified with a hand-held reamer. Power reaming is initiated with a conical reamer. The reamer is advanced slowly within the canal until the proximal cutting edge is at the level of the calcar. As the reamer is withdrawn, lateral pressure is exerted to insure proper lateralization within the canal. Reaming proceeds in one millimeter or two millimeter increments depending on the bone density. Once the appropriate conical reamer has been passed, rasping is initiated. The rasp should be oriented so that the mediolateral axis of the rasp is parallel to the anatomic mediolateral axis of the femoral neck. The rasp is impacted until it is slightly below the level of the initial calcar cut. Subsequently, larger rasps are used until the final rasping is completed with the appropriate size. With the proper size rasp in place, the calcar is planed flush by using the calcar trimmer. With the final rasp still in place, provisional heads/necks are selected to determine the appropriate neck length in order to restore the lateral offset. Trial reduction is carried out to assure that proper leg length and stability are achieved. The stem corresponding to the size of the final rasp used is threaded onto the stem inserter/extractor and impacted into a fully seated position. The collar should seat flush against the medial calcar and the lateral shoulder should seat against the femoral head. After fully seating the femoral component, the appropriate modular head is impacted into the femoral neck. The hip is now ready to be reduced.

Presently, there are various hip replacement systems wherein a polymeric lining is used on the socket component. The metallic ball is received within this polymeric lining. The intention of the polymeric lining is to provide a very smooth and low friction movement between the metallic ball and the wall of the socket. Unfortunately, the repeated contact between the metallic surface of the ball member and the polymeric lining of the socket becomes worn over time. A need exists for being able to provide a lubricant into the space between the exterior surface of the ball member and the polymeric lining of the socket component. There is a general reluctance to use hydrocarbon-based lubricants in view of the potential incompatibility with the human body.

Other hip prosthesis have utilized polymeric linings located between a metallic shell and a metallic shaft of the stem portion of the prosthesis. The purpose of the lining is to allow the prosthesis to better conform to the movement of the human body and also to provide a cushioning effect between the metallic shell and the metal shell of the stem portion. It has been found that, over time, the polymeric lining within the stem portion can become worn so that replacement is required.

In the past, various patents have related to hip replacement operations and to hip prosthesis.

U.S. Pat. No. 3,748,662, issued on Jul. 31, 1973 to A. J. Helfet, describes a surgical procedure for replacing the natural components of a bicondylar joint in a human limb. The prosthetic implant has two pairs of coacting male and female condylar components. The male and female components which replace the natural lateral condyles are spherical or spheroidal in shape to simulate a ball and sock joint. Both male components and both female components can be formed on respective rigid carriers or they may optionally be separate for individual fixation to the patient's limb.

U.S. Pat. No. 3,894,297, issued on Jul. 15, 1975 to Mittelmeier et al., describes a hip joint prosthesis which comprises a substantially frustoconical acetabulum member provided with supporting ribs in the form of a tapering thread and a prosthesis shaft provided with circular supporting ribs allowing anchorage of the prosthesis and the acetabulum member without using a cement or other adhesive.

U.S. Pat. No. 4,187,559, issued on Feb. 12, 1980 to Grell et al., describes a body joint endoprosthesis including an anchoring member having a shaft anchored in a first bone and a pivot member connected to the anchoring member by a pivot joint. The pivot member includes a first body joint member and a support element that bears against a seating surface of the first bone. The first body joint member and the second body joint member are connected to the second bone so as to form the body implant joint.

U.S. Pat. No. 4,355,427, issued on Oct. 26, 1982 to W. Schneider, describes an artificial humerus head having a groove in its exterior surface for receiving the long biceps tendon. A cover bridges the groove to form an elongated open-end channel for the tendon and makes it possible to arrange the long biceps tendon in the channel without separation thereof from the head.

U.S. Pat. No. 4,530,115, issued on Jul. 23, 1985 to Muller et al., describes a shank for a prosthesis which is composed of a blade which carries a joint head and a wedge-shaped end piece. The end piece is driven in along a guide in the lateral narrow side of the blade while the blade remains in a fixed position. The wedge-shaped form of the end piece permits fixation of the blade at a predetermined height such that the joint head can be at the level of the trochanter tip.

U.S. Pat. No. 4,775,381, issued on Oct. 4, 1988 to Tari et al., describes a hip prosthesis formed with a conventional head provided with a spherical shape, a neck, and a stem. A guide profile is formed along the outer straight side of the stem and contains components which are parallel with the side. The guide profile fits the inner surface of the medullary cavity nail so as to allow the simultaneous use of the hip prosthesis and the medullary cavity nail and the nailing of the already prosthetized femur.

U.S. Pat. No. 5,026,399, issued on Jun. 25, 1991 to Engelbrecht et al., describes a prosthetic device for the partial or total replacement of a bone, such as a femur. The prosthesis has a rod-like bridging member which spans the major part of the gap between the two joints. An abutment member is mounted at either end of the bridging member and each of the abutment members engages a bone adjacent that which is to be partially or totally replaced. Each of the abutment members may constitute part of an artificial joint. The abutment members may be rotatable relative to one another and to the bridging member about the longitudinal axis of the latter in order that the abutment members may assume a relative angular orientation best suited to the characteristics of the patient.

U.S. Pat. No. 5,702,457, issued on Dec. 30, 1997 to Walsh et al., describes a humeral prosthesis including a shank having a metaphyseal part having a housing therein with a semi-spherical portion in which housing is introduced a sphere to which is secured a bearing surface hemispherical cap adapted to be received within the glenoid cavity of a shoulder. A securing element is provided which extends through the metaphyseal part of the shank for securing the sphere within the housing at a predetermined position with respect to the shank.

U.S. Pat. No. 5,725,597, issued on Mar. 10, 1998 to S. K. Hwang, describes an artificial hip joint having a construction capable of reducing abrasion of a polyethylene layer formed within the acetabulum cup when the head of the femur pivots in the acetabulum cup. The artificial acetabulum cup is implanted in the acetabulum of a user's pelvic bone and includes a hollow hemispherical member made of a metal. The polyethylene layer is formed on the inner surface of the hemispherical member. A femoral head holder is fixed to the femur. The femur head holder includes a spherical metal femur head pivotally held in the artificial acetabulum cup. A shaft is coupled at an upper end thereof to the femoral head and adapted to support the femoral head. A housing extends inclinedly through the greater trochanter of the femur and adapted to receive the shaft therein in such a manner that it rotates with respect to the shaft. Bearings are mounted between the shaft and the housing and are adapted to support axially and radial loads applied to the shaft at the femur head by the weight of the user.

It is an object of the present invention to provide a joint replacement system which is self-lubricating.

It is another object of the present invention to provide an hip replacement system which minimizes wear-and-tear between the ball component and the socket component.

It is another object of the present invention to provide an hip replacement system which allows the introduction of a human-based lubricant into the area between the ball component and the socket component.

It is still a further object of the present invention to provide a hip replacement system which allows lubricant to be introduced into the spaces located between metallic components and polymeric components of the hip replacement system.

It is a further object of the present invention to provide a hip replacement system which allows the human-based lubricant to be introduced, from time to time, into the system.

It is a further object of the present invention to provide a hip replacement system which maximizes the capability of the hip replacement system with the human body.

These and other objects and advantages of the present invention will become apparent from a reading of the attached specification and appended claims.

BRIEF SUMMARY OF THE INVENTION

The present invention is a hip replacement system comprising a socket having a generally hemispherical cavity therein, a ball member cantably affixed within the socket and having an exterior surface positioned within the generally hemispherical cavity of the socket, a stem affixed to the ball member and extending outwardly therefrom, and a lubricant located within a channel formed in the stem. The exterior surface of the ball member has at least one opening therein communicating with an interior of the ball member. The stem has the channel in communication with this opening on the ball member.

In the preferred embodiment of the present invention, the lubricant is compressed body fat. This body fat extends through the channel so as to fill a space between the exterior surface of the ball member and an interior surface of the socket. An inlet is connected to the channel and extends outwardly of the stem. This inlet allows the lubricant to be introduced into the channel. The inlet is a catheter having a one-way valve secured thereto.

In the preferred embodiment of the present invention, the socket includes a metallic exterior body having an interior surface, and a polymeric lining affixed to the interior surface of the socket. The ball member is juxtaposed against the polymeric lining. A seal is affixed to the end of the socket for retaining the lubricant in the space between the exterior surface of the ball member and the interior surface of the socket. The seal is an annular gasket having an inner edge juxtaposed against the exterior surface of the ball member.

In the preferred embodiment of the present invention, the stem comprises a metallic shell, a polymeric lining extending along an interior surface of the metallic shell, and a metallic shaft positioned interior of the polymeric lining. The channel is formed between the shaft and the polymeric lining. A seal is affixed to the top of the shell for preventing the lubricant from passing outwardly from the stem. The shaft has a neck portion extending outwardly of the shell. The ball member is affixed to the neck portion. The channel will extend along the neck portion.

The socket is affixed within an acetabulum area of the human body. The stem is affixed within the femur of the human body. The lubricant is fat from the same human body.

DETAILED DESCRIPTION OF THE INVENTION

Figure 1:
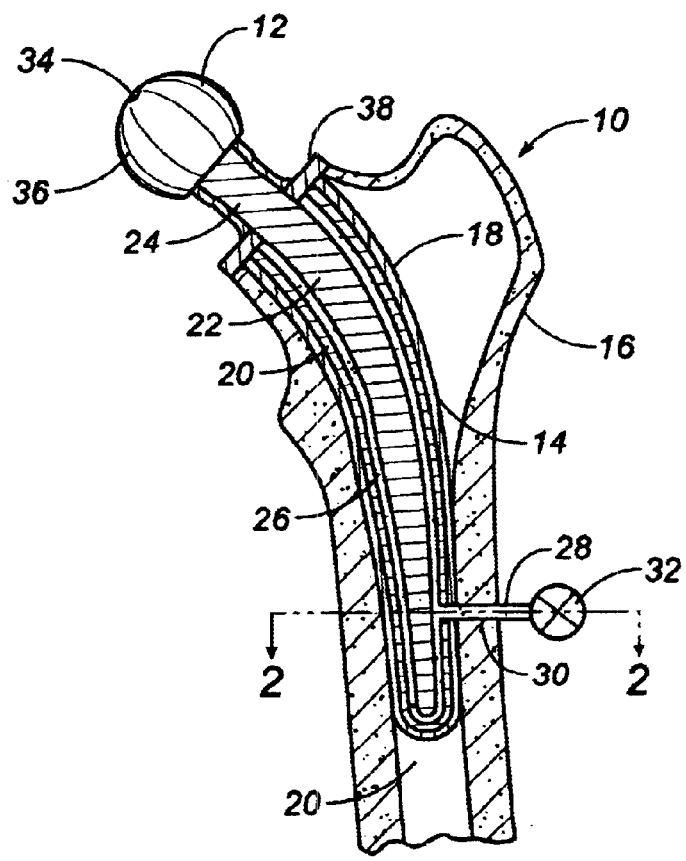
FIG. 1 is a cross-sectional view showing the preferred embodiment of the present invention.

Referring to FIG. 1, there is shown at 10 the hip replacement system in accordance with the teachings of the present invention. The hip replacement system 10 includes a socket (shown in detail in FIGS. 3–5), a ball member 12, a stem 14, and a lubricant (shown in later drawings). In FIG. 1, it can be seen that the stem 14 is placed within the upper portion of a femur 16 of the leg. In particular, the stem 14 includes a metallic shell 18 extending downwardly into the interior 20 of the femur 16. The metallic shell 18 can be suitably secured to the femur 16 by surgical nails, screws or by other means. The metallic shell 18 will provide a secure fit for the stem 14 within the femur 16. A polymeric lining 20 will extend along the interior surface of the metallic shell 18 of the stem 14. A metallic shaft 22 extends interior of the polymeric lining 20 and along the length of the shell 18. The shaft 22 has a neck 24 extending outwardly of the femur 16 for securing to the ball member 12.

Importantly, in the present invention, a channel 26 extends within the stem 14 between the metallic shaft 22 and the polymeric lining 20. Channel 26 will be filled with a suitable lubricant. The lubricant is introduced by way of inlet 28. Inlet 28 includes a catheter 30 that has a one-way valve 32 positioned thereon. In the preferred embodiment of the present invention, the inlet 28 is known as a "PORTA-CATH" (TM). The inlet 28 will extend through the femur 16 so as to have an opening on the leg. As such, as needed, the lubricant can be introduced through the one-way valve 32, through the catheter 30 and into the channel 26.

In the present invention, the ball member 12 is positioned at the top of the neck 24 of the shaft 22 associated with the stem 14. The ball 12 has a small opening 34 located at its upper end thereof. When installed into the socket, the opening 34 will allow the lubricant to pass into the space between the exterior surface 36 of the ball member 12 and the inner wall of the socket. The channel 26 will communicate through the stem 14 and the neck 24 with the opening 34 so as to allow the lubricant to pass into the space between the ball member and the socket.

A seal 38 is positioned at the top of the shell 18 and around the shaft 22. The seal 38 serves to retain the lubricant within the channel 26 and to prevent the lubricant from emerging outwardly of the shell 18. The seal 38 facilitates the ability of the lubricant to migrate through the channels associated with the neck 24 of the shaft 22. The seal 38 is positioned at the top open end of the femur 16.

In the present invention, it is important to note that the lubricant is compressed body fat. This compressed body fat can be obtained by suitable and conventional surgical techniques, such as liposuction. Since it is the body fat of the same person that has the femur 16, there will be absolute capability between the lubricant and the person having the hip replacement system 10. There is no difficulty if the body fat should migrate from the area between the ball member 12 and the socket. Since body fat is always available, more lubricant can be supplied, as required. As such, the present invention is able to utilize body fat as the lubricant instead of polymeric materials and/or hydrocarbon-based lubricant. Additionally, by filling the channel 26 between the shaft 22 and the polymeric lining 20 of the stem 14, the lubricant within the channel 26 will reduce the possibility of deterioration of the polymeric lining throughout continued use.

Figure 2:
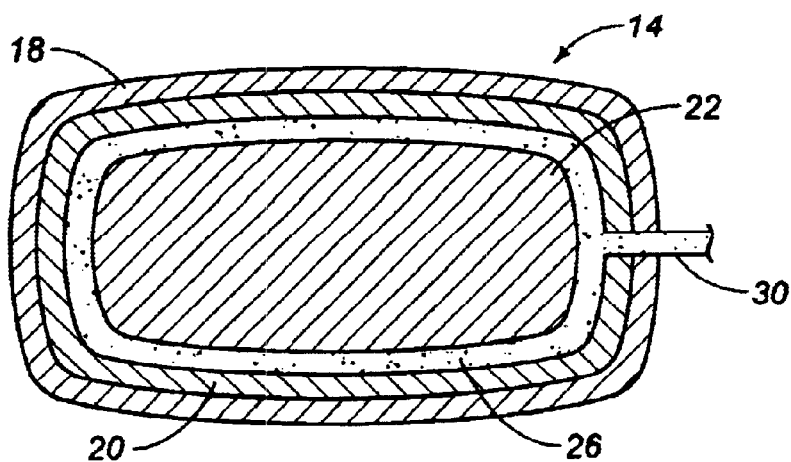
FIG. 2 is a cross-sectional view taken across lines 2—2 of FIG. 1.

FIG. 2 shows a cross-sectional view of the stem 14. In particular, it can be seen that the stem 14 has a metallic shell 18, a polymeric lining 20 and an interior metallic shaft 22. The channel 26 extends around the shaft 22. In FIG. 2, the channel 26 is filled with lubricant 40. The catheter 30 is through the shell 18 and the lining 20 so as to communicate with the channel 26.

Figure 3:
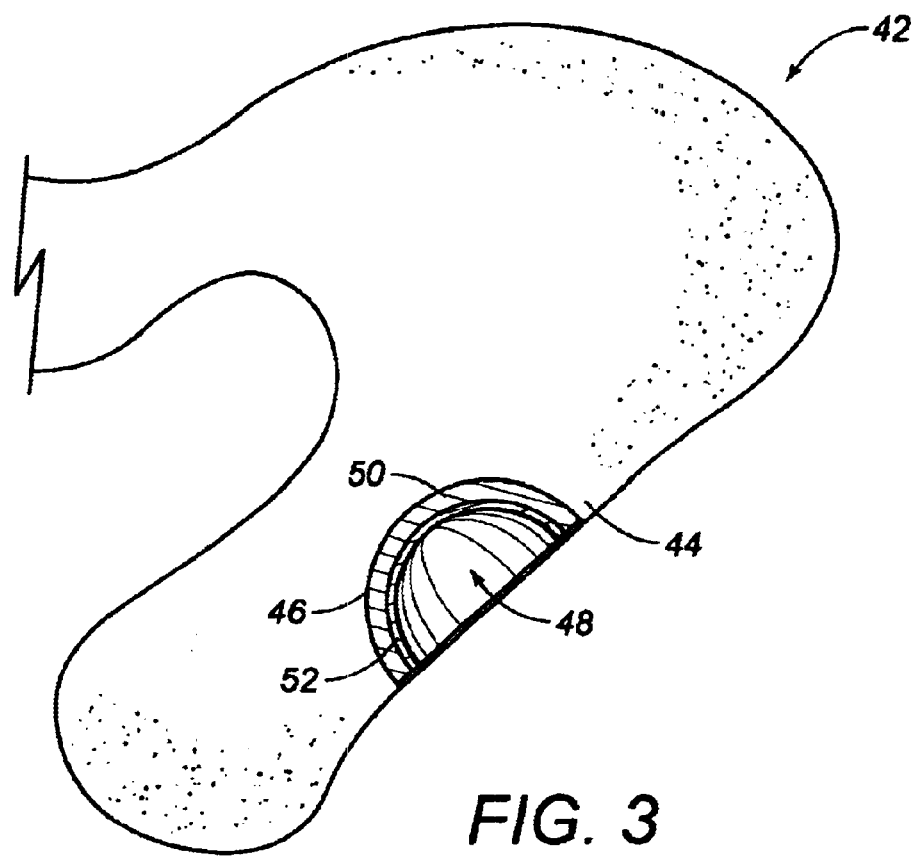
FIG. 3 is a cross-sectional view showing the placement of the socket into the acetabulum area of a hip.

FIG. 3 shows the human hip 42 having the acetabulum area 44. The socket 46 is placed within the acetabulum area 44. Typically, the socket 46 is secured in its desired position through the use of surgical nails, screws or other means. The socket 46 will have a hemispherical cavity 48 formed therein and facing the exterior of the acetabulum area 44.

In FIG. 3, it can be seen that the socket 46 has a shell 50 which is secured to the hip 42. A polymeric lining 52 extends around the inner wall of the shell 50. Conventionally, in past procedures, the polymeric lining 52 would provide a smooth contact surface between the metallic ball member 12 and the socket 46. However, it has been noted that, after continued use, the metallic ball member 12 will cause deterioration of the polymeric lining 52 to the detriment of the user.

Figure 4:
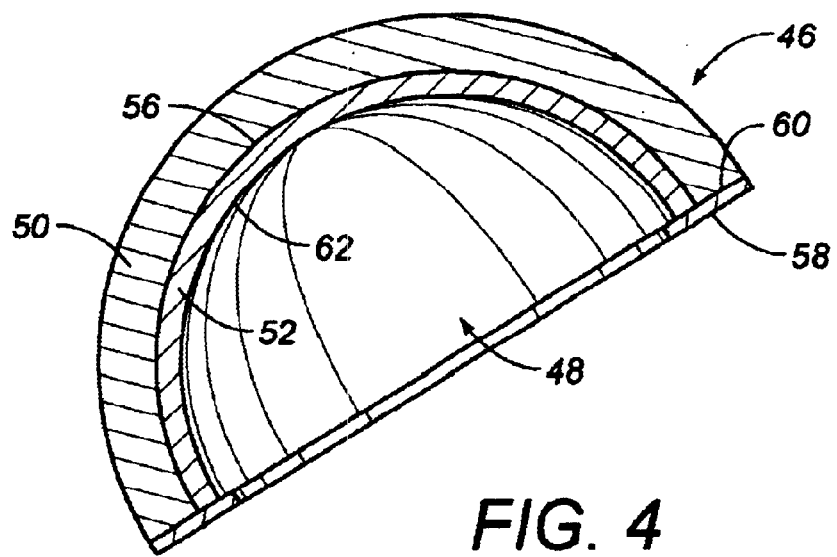
FIG. 4 is an enlarged and detailed cross-sectional view showing the socket of the present invention.

FIG. 4 shows a detailed view of the socket 46. As can be seen, the socket 46 has hemispherical cavity 48 formed therein. The polymeric lining 52 is positioned against the inner surface 56 of the metallic shell 50. A sealing member 58 is affixed to the end 60 of the metallic shell 50 and over the end of the polymeric lining 52. The sealing member 58 will be in the nature of an annular gasket which is properly positioned so as to retain the lubricant in the space between the exterior surface of the ball member 12 and the inner surface 62 of the polymeric lining 52.

Figure 5:
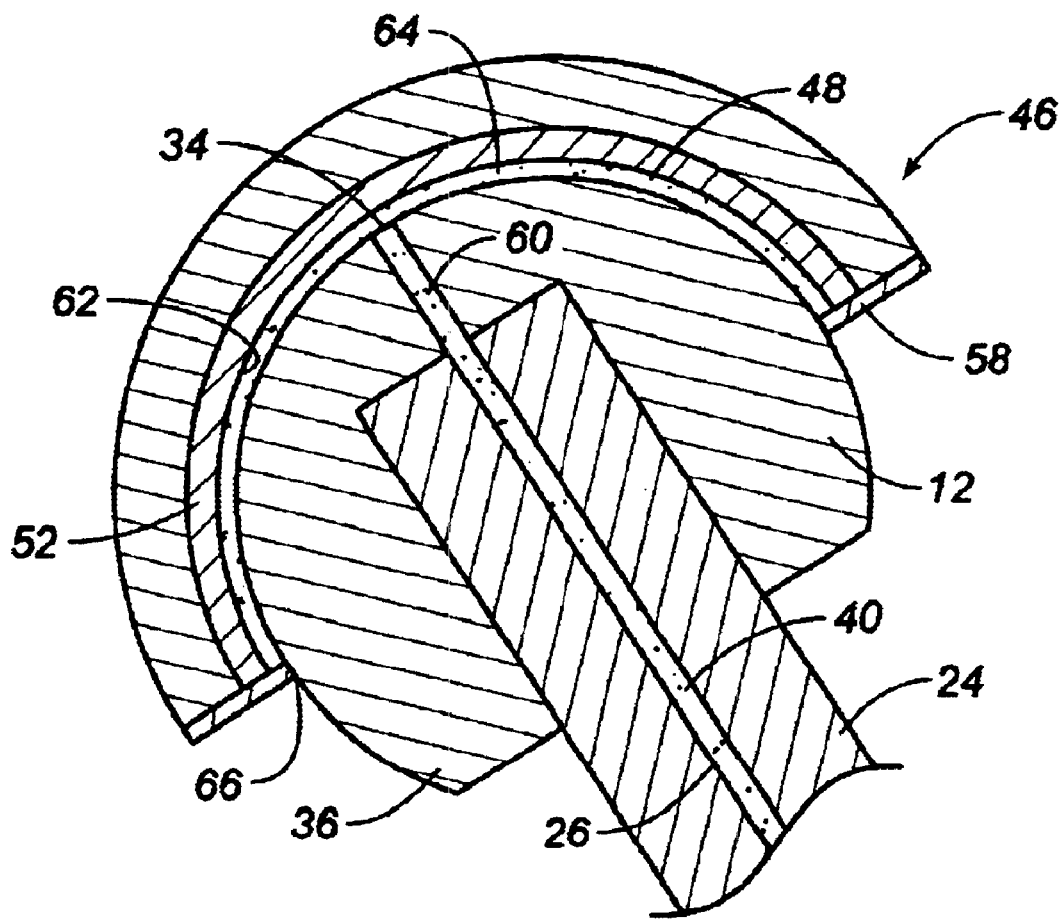
FIG. 5 is a cross-sectional view showing the placement of the ball member within the socket of the present invention.

FIG. 5 shows how the ball member 12 is received within the hemispherical cavity 48 of the socket 46. In particular, in FIG. 5, it can be seen that the neck portion 24 of the shaft 22 has channel 26 extending therethrough. The channel 26 allows the lubricant 40 to flow toward the opening 34 on the ball member 12. A channel 60 is formed in the ball member 12 so as to allow the lubricant 40 to properly flow from the channel 26 to the opening 34. Within the concept of the present invention, it is possible that a plurality of openings 34 can be formed on the exterior surface of the ball member 12 so as to allow the lubricant 40 to flow into the space 64 between the exterior surface 36 of the ball member 12 and the inner wall 62 of the lining 52. The gasket 58 is illustrated as having its inner edge 66 juxtaposed against the exterior surface 34 of the ball member 12. The gasket 58 serves to retain the lubricant 48 in the space 64.

In the configuration of the present invention, the lubricant 40 can be continually provided to the space 64 so as to assure a long life for the hip replacement 10 of the present invention. When friction starts to occur between the exterior surface 36 of the ball member 12 and the inner wall 62 of the lining 52, additional lubricant can be introduced into the channel 26 by simply passing the lubricant through the inlet 28 and into the channel 26 of the stem 14. By using body fat, the lubricant will be absolutely compatible with the human body.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A hip replacement system comprising:
    a socket having a generally hemispherical cavity therein;
    a ball member cantably affixed within said socket, said ball member having an exterior surface positioned within said generally hemispherical cavity of said socket, said exterior surface having at least one opening therein communicating with an interior of said ball member;
    a stem affixed to said ball member and extending outwardly therefrom, said stem having a channel therein in communication with said opening on said ball member; and
    a lubricant located within said channel of said stem, said lubricant being body fat.

2. The system of claim 1, said body fat being compressed body fat.

3. The system of claim 1, said body fat extending through said channel so as to fill a space between said exterior surface of said ball member and an interior surface socket.

4. The system of claim 1, further comprising:
    an inlet means connected to said channel and extending outwardly of said stem, said inlet means for allowing said lubricant to be introduced into said channel.

5. The system of claim 4, said inlet means comprising:
    a catheter having a valve secured thereto, said valve being a one-way valve suitable for preventing the lubricant from being released from said channel.

6. The system of claim 1, said socket comprising:
    a metallic exterior body having an interior surface; and
    a polymeric lining affixed to said interior surface of said metallic exterior body, said ball member juxtaposed against said polymeric lining.

7. The system of claim 6, further comprising:
    a sealing means affixed to an end of said socket for retaining said lubricant in a space between said exterior surface of said ball member and said interior surface of said socket.

8. The system of claim 1, said socket adapted to be affixed within an acetabulum area of a human body, said stem adapted to be affixed within a femur of the human body said lubricant being fat from the human body.

9. The system of claim 8, further comprising:
    an inlet means connected to said channel so as to allow said fat to be introduced into said channel, said inlet means having an opening adapted to open exterior of the human body.

10. The system of claim 8, said fat filling a space between said exterior surface of said ball member and a wall of said hemispherical cavity of said socket.

11. A hip replacement system comprising:
    a socket having a generally hemispherical cavity therein;
    a ball member cantably affixed within said socket, said ball member having an exterior surface positioned within said generally hemispherical cavity of said socket, said exterior surface having at least one opening therein communicating with an interior of said ball member;
    a stem affixed to said ball member and extending outwardly therefrom, said stem having a channel therein in communication with said opening on said ball member; and
    a lubricant located within said channel of said stem, said socket comprising:
        a metallic exterior body having an interior surface; and
        a polymeric lining affixed to said interior surface of said metallic exterior body, said ball member juxtaposed against said polymeric lining; and
    a sealing means affixed to an end of said socket for retaining said lubricant in a space between said exterior surface of said ball member and said interior surface of said socket, said sealing means being an annular gasket having an inner edge juxtaposed against said exterior surface of said ball member.

12. The system of claim 9, said channel formed between said stem and said polymeric lining.

13. The system of claim 9, further comprising:
    a sealing means affixed to a top of said shell for preventing said lubricant from passing outwardly from said stem.

14. The system of claim 9, said stem having a neck portion extending outwardly of said shell, said ball member being affixed to said neck portion, said channel extending along said neck portion.

15. A joint replacement system comprising:
    a socket having a polymeric lining;
    a ball member cantably affixed within said socket, said ball member having an exterior surface within said socket, said exterior surface having an opening thereon;
    a stem affixed to said ball member and extending outwardly therefrom, said stem having a channel therein in communication with said opening on said ball member;
    a lubricant received within said channel of said stem and extending into a space between said exterior surface of said socket and said polymeric lining of said socket; and
    an inlet means connected to said channel and extending outwardly of said stem, said inlet means for allowing said lubricant to be introduced into said channel.

16. The system of claim 15, said lubricant being body fat.

17. The system of claim 15, said stem comprising:
    a metallic shell;
    a polymeric lining extending along an interior surface of said metallic shell; and
    a metallic shaft positioned interior of said polymeric lining, said channel formed between said shaft and said polymeric lining, said ball member being affixed to a stem extending from said metallic shaft outwardly of said metallic shell.

* * * * *